United States Patent
Philipp et al.

(10) Patent No.: US 8,016,875 B2
(45) Date of Patent: Sep. 13, 2011

(54) MEDICAL IMPLANT, IN PARTICULAR STENT FOR USE IN BODILY LUMEN

(75) Inventors: Jens Philipp, Berlin (DE); Andreas Neumann, Berlin (DE)

(73) Assignee: Biotronik VI Patent AG, Baar (CG)

( * ) Notice: Subject to any disclaimer, the term of this patent is extended or adjusted under 35 U.S.C. 154(b) by 230 days.

(21) Appl. No.: 12/116,393

(22) Filed: May 7, 2008

(65) Prior Publication Data
US 2008/0281400 A1    Nov. 13, 2008

(30) Foreign Application Priority Data
May 9, 2007   (DE) .......................... 10 2007 021 692

(51) Int. Cl.
*A61F 2/82* (2006.01)
(52) U.S. Cl. ...................................... 623/1.15; 623/1.42
(58) Field of Classification Search ................. 623/1.11, 623/1.15, 1.34, 1.39, 1.42, 1.44; 600/400; 340/10.1, 572.1, 572.5
See application file for complete search history.

(56) References Cited

U.S. PATENT DOCUMENTS

| | | | |
|---|---|---|---|
| 6,280,385 B1 * | 8/2001 | Melzer et al. ................. | 600/423 |
| 2004/0082867 A1 | 4/2004 | Esch et al. | |
| 2004/0254632 A1 | 12/2004 | Alt et al. | |
| 2005/0159802 A1 | 7/2005 | Furst et al. | |
| 2006/0105016 A1 * | 5/2006 | Gray et al. ..................... | 424/423 |
| 2007/0032861 A1 * | 2/2007 | Weber et al. ................. | 623/1.34 |

FOREIGN PATENT DOCUMENTS

| | | |
|---|---|---|
| DE | 19746735 A1 | 4/1999 |
| EP | 1023609 | 8/2000 |
| WO | 0112092 A1 | 2/2001 |
| WO | 2005027785 A2 | 3/2005 |
| WO | 2006083478 A1 | 10/2006 |
| WO | 2007109756 A2 | 9/2007 |

OTHER PUBLICATIONS

Search Report for German Patent Application No. 10 2007 021 692.2; Oct. 19, 2007.
Search Report and Written Opinion for European Patent Application No. 08075256.1; Sep. 2, 2009.

* cited by examiner

*Primary Examiner* — Thomas J Sweet
*Assistant Examiner* — Seema Swaminathan
(74) *Attorney, Agent, or Firm* — Jason A. Bernstein; Barnes & Thornburg LLP

(57) ABSTRACT

A medical implant, in particular a stent for insertion in a bodily lumen, having a base structure (2, 3), wherein a passive electronic oscillating circuit configuration (4), comprising at least one inductor (L) and at least one capacitor (C1 through C4), is integrated in the base structure (2, 3), whose natural frequency ($f_{res0}$) in the implanted state of the implant (1) is externally detectable by exciting the oscillating circuit configuration (4) using electromagnetic radiation such that a significant identification feature or a change of the base structure (2, 3) is detectable by the value or a change of the natural frequency ($f_{res0}$) of the oscillating circuit configuration (4).

21 Claims, 9 Drawing Sheets

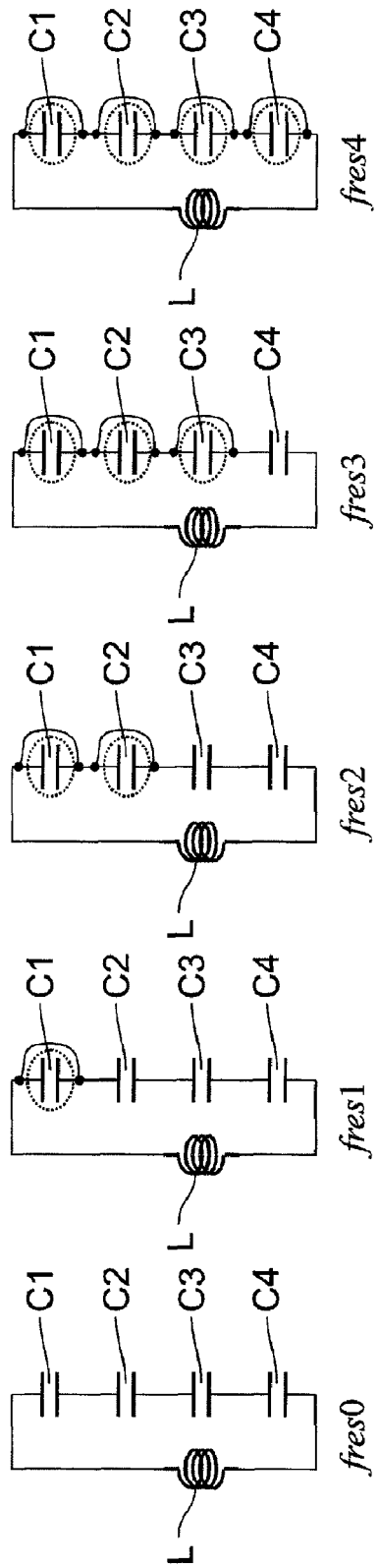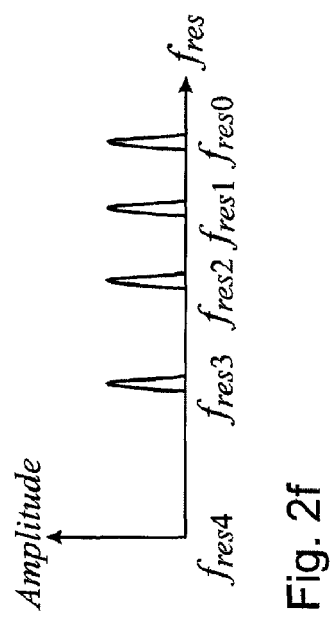

MEDICAL IMPLANT, IN PARTICULAR STENT FOR USE IN BODILY LUMEN

PRIORITY CLAIM

This patent application claims priority to German Patent Application No. 10 2007 021 692.2, filed May 9, 2007, the disclosure of which is incorporated herein by reference in its entirety.

FIELD

The present disclosure relates to a medical implant and, in particular, a stent for use in a bodily lumen.

BACKGROUND

Implantable stents are used, for example, for the treatment of stenoses in coronary vessels with the aid of a catheter. Other areas of application of implants of this type are, for example, so-called aneurysm coils.

With implants of this type, the fundamental problem exists after the implantation when the state of the implant must be able to be monitored, in particular, in the chronological behavior after the insertion. For this purpose, the use of imaging methods is known, such as an x-ray examination in which contrast agent must often be injected for better display of the implant. Both the x-ray radiation strain and also the application of the contrast agent represent undesirable strains for the body of the patient. Furthermore, the state of implants, which particularly comprise metal alloys having a predominant proportion of elements of low atomic number (such as magnesium) is hardly detectable fundamentally using angiography.

Various goals are desirable in connection with monitoring the implant. Thus, establishing damage, such as breaking off of struts of the base structure of the implant or recognizing strut cracks, is of interest, in particular, in nondegradable implants.

In degradable implants, the current degradation state of the implant and the time curve of the degradation are important items of information.

Finally, implants having medication depots are also to be cited, in which an important complex of questions comprises whether the deposited medication has already been released and to what degree release of the deposited medication has already occurred.

The examination methods based on x-ray markers and contrast agents referenced hereinabove may only provide little information and, as noted, are stressful to patients.

The fundamental possibility of applying active sensors to the implant, such as a stent, has been discussed in the prior art. However, use of active sensors applied to the implant is not possible, particularly with biodegradable stents, because sensors of this type are based on semiconductor materials which are nondegradable and typically also contain toxic materials, for example, due to the doping of the semiconductor material.

SUMMARY

The present disclosure describes several exemplary embodiments of the present invention.

One aspect of the present disclosure provides a medical implant, in particular a stent for use in a bodily lumen, comprising a base structure having a passive electronic oscillating circuit configuration wherein at least one inductor and at least one capacitor is integrated in the base structure, whose natural frequency in the implanted state of the implant is externally detectable by exciting the oscillating circuit configuration using an electromagnetic radiation in such a way that a significant identification feature or a change of the base structure is detectable by the value or a change of the natural frequency of the oscillating circuit configuration.

The present disclosure equips a medical implant in such a way that the state of the implant is detectable using comparatively simple technical means without the stressful examination methods.

The implant itself is quasi-"repurposed" into a passive electromagnetic oscillating circuit, which may be "scanned" by medically harmless electromagnetic radiation. The design according to the present disclosure is thus not a hybrid solution, in which an oscillating circuit made of components intended separately for this purpose is attached to the stent. Rather, the state itself forms the oscillating circuit. It is thus to be referred to, figuratively speaking, as a "stent having passive intelligence".

The base structure of stents may comprise supporting and nonsupporting elements, the present disclosure being able to be implemented in both types of these elements.

According to one exemplary embodiment of the present disclosure, the natural frequency of the oscillating circuit configuration may be significant for the model and even the serial number of the implant. This is implemented, for example, in that an implant of a specific model is constructed having an oscillating circuit configuration of a natural frequency representative thereof, which may be externally scanned after the implantation.

According to a further exemplary embodiment, damage to the base structure may be concluded from a change of the natural frequency of the oscillating circuit configuration after the implantation of the implant. This occurs, for example, if a strut of the base structure forming a capacitor breaks off, the oscillating circuit is interrupted and a natural frequency is thus no longer measurable.

An exemplary embodiment in which a change of the natural frequency of the oscillating circuit configuration after the implantation of the implant is significant for the amount of biodegradation of the base structure is of special interest for application. In this case, one, or preferably multiple, capacitors are connected together with at least one inductor to form an oscillating circuit, the envelope of the implant being formed by a biodegradable insulation which covers the oscillating circuit configuration. With the progressing decomposition of this insulation, the capacitors are gradually exposed to the physiological, electrically conductive liquid flowing in the bodily lumen so that the corresponding capacitor is short-circuited. Each short-circuit of a capacitor then changes the total capacitance of the capacitors connected in series and thus the natural or resonance frequency of the oscillating circuit. The natural frequency is thus determined by the still intact, insulated capacitors. The short-circuit of a capacitor thus acts practically like a switch which removes the capacitor from the series circuit, by which the natural frequency is suddenly changed.

To be able to track the degradation behavior as precisely as possible in this context, it is advantageous if each capacitor "switches", i.e., is short-circuited, at a different and approximately defined time after the implantation. This may be set during the production by a variation of the insulation thickness on each capacitor, for example. Alternatively thereto, it is also possible to vary the density of the insulation material or the type of material itself. By suitable dimensioning of the capacitors, it may be uniquely established, if necessary, which capacitor has already short-circuited. If it is only necessary to know how many capacitors have short-circuited, identical dimensioning for all capacitors is sufficient, as explained in greater detail below in the exemplary embodiment.

According to a further exemplary embodiment of the present disclosure, a change of the natural frequency of the oscillating circuit configuration after the implantation of the implant may be significant for the status of a medication depot, which is integrated in the implant and degrades with a time delay. For this purpose, as explained in greater detail in the exemplary embodiment, a capacitor is, in turn, to be assigned suitably to the medication depot, which is exposed synchronously because of the degradation of the medication depot and thus correspondingly changes its capacitance, which in turn acts on the natural frequency of the oscillating circuit in an externally detectable way.

The inductor of the oscillating circuit configuration is preferably formed by an electrically conductive strut of the base structure. This may be implemented easily because struts of this type typically run around the periphery and thus already form a coil winding based on their fundamental shaping.

The at least one capacitor of the oscillating circuit configuration is preferably implemented by a layered construction of a strut of the base structure. The strut accordingly comprises an internal insulation layer, a first electrically conductive layer as the first capacitor pole, an intermediate layer preferably implemented as a dielectric material, a second electrically conductive layer as the second capacitor pole, and an external insulation layer possibly comprising biodegradable material. This is described in greater detail in the exemplary embodiment.

An external scanning device may be used for scanning the oscillating circuit which emits a variable electromagnetic radiation to excite the oscillating circuit. Suitable frequency ranges for transmitting electromagnetic signals through the human body are in the range from a few kilohertz up to approximately 5 GHz, the structure sizes of the implant to be used predefining a narrower range. In the exemplary embodiment below, the resonance range is between approximately 300 MHz and approximately 700 MHz.

For example, a frequency sweep generator may be used in the scanning device, which covers the entire possible frequency band in which the natural frequency of the oscillating circuit configuration lies depending on the state of the passive components participating therein. The scanning device then detects the resonance response of the oscillating circuit configuration. The scanning device may thus obtain corresponding significant information on the basis of the value of the resonance response of the implant. In the event of multiple stents having "passive intelligence" lying close together in the body, it is advantageous for the directional characteristic of the transmitter operating in the scanning device to be bundled as much as possible.

Alternatively to an external scanning device, an active medical implant, such as a cardiac pacemaker, defibrillator, medication pump, neurostimulator, and the like, may also be equipped with a corresponding transceiver device. This is advantageous, in particular, for known implants having telemedical data transmission. These so-called "transceivers" may be modified in such a way that they may cover the desired frequency range of the oscillating circuit configuration.

In summary, a well reproducible scanning characteristic may be achieved in regard to the quasi-digital switching behavior of the at least one capacitor by its short-circuiting upon exposure to the conductive physiological fluid in the area of the stent. Each short-circuit of a capacitor generates a significant jump of the resonance frequency, the configuration being very tolerant to manufacturing irregularities. Varying values of the participating components of the oscillating circuit do change the resonance frequencies, but as long as these deviations have an amount remaining significantly below the frequency shift between two resonance frequencies, this does not represent a problem which threatens the functional capability of the configuration.

BRIEF DESCRIPTION OF THE DRAWINGS

Various aspects of the present disclosure are described hereinbelow with reference to the accompanying figures.

FIG. 2a shows a replacement circuit diagram of an oscillating circuit configuration, integrated in the stent, in a short-circuit situation;

FIG. 2b shows a replacement circuit diagram of an oscillating circuit configuration, integrated in the stent, in a second short-circuit situation;

FIG. 2c shows a replacement circuit diagram of an oscillating circuit configuration, integrated in the stent, in a third short-circuit situation;

FIG. 2d shows a replacement circuit diagram of an oscillating circuit configuration, integrated in the stent, in a fourth short-circuit situation;

FIG. 2e shows a replacement circuit diagram of an oscillating circuit configuration, integrated in the stent, in a fifth short-circuit situation;

FIG. 2f shows a frequency diagram of the resonance responses of the oscillating circuit in the various short-circuit situations as shown in FIGS. 2a-2e;

DETAILED DESCRIPTION

Figure 1A:
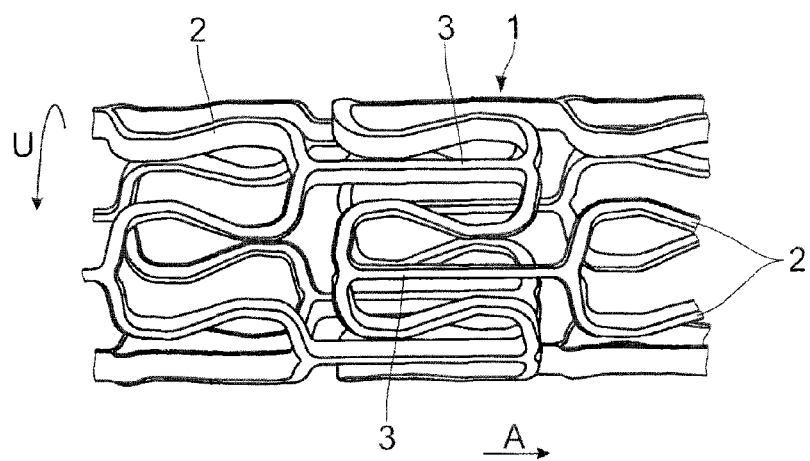
FIG. 1a shows a detail view of a stent having "passive intelligence"

The basic structure of the stent 1 shown in detail in FIG. 1 comprises meandering struts 2 running around the circumference and axial connectors 3 connecting them. The present disclosure does not relate in this context to the special shaping of the struts 2 and axial connectors 3, rather the present disclosure is implemented within the construction of the struts 2 or axial connectors 3, as will be explained in the following.

Figure 1B:
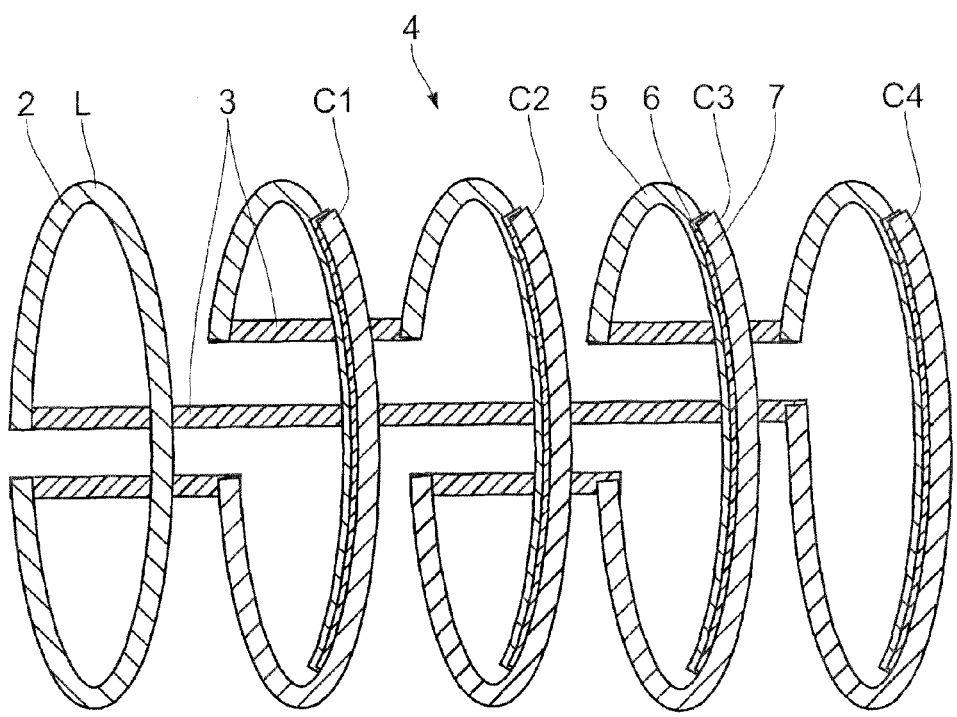
FIG. 1b shows a schematic perspective illustration of an oscillating circuit configuration.

As indicated in FIG. 2a, a passive electronic oscillating circuit configuration 4 is integrated in the stent 1 by a construction (explained in greater detail hereinbelow) of the struts 2 and/or axial connectors 3, which comprises an inductor L and capacitors C1 through C4 in a series circuit. As schematically indicated in FIG. 1b, the capacitors C1 through C4 and the inductor L may be implemented by an appropriate implementation of the strut identified as a whole by 2. The individual capacitors C1 through C4 fundamentally comprise an internal electrically conductive layer 5 in the form of a partial ring, an insulating intermediate layer 6 implemented as a dielectric material, and a second electrically conductive layer 7 in the form of a partial ring, which overlaps at least partially with the intermediate layer 6 and the internal layer 5. These individual capacitor configurations C1 through C4 are electrically connected in series to one another in the axial direction A via the axial connectors 3. The oscillating circuit configuration 4 is completed by the inductor L, which comprises an electrically conductive strut 2 led around the circumference U of the stent.

In the initial state, this fundamental oscillating circuit configuration is enclosed in an insulating, biodegradable envelope by whose degradation the individual capacitors C1 through C4 are significantly exposed and thus short-circuited by blood flowing around the stent, for example. This is indicated in FIGS. 2a-2e.

In the following, the design of the capacitors C1 through C4 and the influence of their short-circuit on the natural frequency of the oscillating circuit configuration 4 are explained in greater detail.

A coronary stent is to be dimensioned using display of its degradation state in 25% steps here as an example. The configuration of the components is schematically shown in FIG. 1b.

The influence of parasitic variables, such as electrical resistances $R_{par}$, capacitances $C_{par}$, and inductances $L_{par}$, is only quantitatively observed here. These may have effects on the resonance frequency $f_{res}$, and the oscillating circuit quality Q. Such parasitic parameters arise, for example, due to the influence of the bodily fluid and the body tissue which enclose the stent. These have an electrical impedance Z resulting from $R_{par}$, $C_{par}$, $L_{par}$, which is coupled to the oscillating circuit. The properties of the oscillating circuit such as the resonance frequency $f_{res}$ and the quality Q are thus influenced. The influence of these parasitic variables must be considered when designing such an implant.

The following calculation is thus idealized.

An air-core coil which runs once around the stent circumference is assumed. The inductance resulting therefrom results as follows:

$$L = \mu \cdot \mu_r \frac{N^2 \cdot A}{h} [H]$$

$$\mu = 4 \cdot \Pi \cdot 10^{-7} \left[\frac{Vs}{Am}\right]$$

$\mu_r = 1$ (water)

$A$ = area of stent cross-section $N$ = number of turns $r = 1 \text{ mm} = 10^{-3} m$ (coronary stent)

$h = 0, 1 \text{ mm} = 10^{-4} m$ $A = \Pi r^2$ $A = \Pi \cdot 10^{-6} [m^2]$ $$L = 4\Pi \cdot 10^{-7} \frac{\Pi \cdot 10^{-6}}{10^{-4}} [H]$$

$$L = 4\Pi^2 \cdot 10^{-9} [H]$$

$$L = 40 \cdot 10^{-9} [H]$$

$$L = 40 \text{ [nH]}$$

To keep the design of the stent and the computing example simple, identical capacitors are assumed here. This means that it may be externally established how many switches have already been closed, but not which switches have been closed. If this is also of interest, the capacitors must have different capacitances. This may occur through variation of the dimensions of the webs, for example.

To ascertain a possible capacitance on a web of a coronary stent, for example, the following structural variables are assumed:

$b = 100 \, [\mu m] = 10^{-4} \, [m]$ width of a stent web $l = 5 \, [mm] = 5 \cdot 10^{-3} [m]$ length of a stent web $d = 10 \, [\mu m] = 10^{-5} [m]$ width of the dielectric material $\varepsilon_0 = 1, 112 \cdot 10^{-10} \left[\frac{F}{m}\right]$ dielectric constant $$C = \frac{\varepsilon_0 \cdot \varepsilon_r \cdot b \cdot l}{d}$$

$$C = \frac{1,112 \cdot 10^{-10} \cdot 5 \cdot 10^{-3} \cdot 10^{-3}}{10^{-4}} [F]$$

$$C = 5,6 \cdot 10^{-12} [F]$$

$C = 5,6$ [pF] per web-capacitor

The natural frequency $f_{res}$ of the stent results as follows:
In general for the resonance frequency:

$$f_{res} = \frac{1}{2\Pi \cdot \sqrt{L \cdot C}} [Hz]$$

If capacitors are connected in series:

$$C_{ges} = \left(\frac{1}{C_1} + \frac{1}{C_2} + \frac{1}{C_3} + \ldots + \frac{1}{Cn}\right)^{-1}$$

Because in this computing example, all capacitors are to have the same value $$C_{ges} = \frac{1}{n}C$$

Using 40 nH for the coil, the formula simplifies to $$f_{resn} = \frac{800}{\sqrt{\frac{1}{n}C}} \text{ [Hz]}$$

The natural frequencies $f_{res4}$, $f_{res3}$, $f_{res2}$, $f_{res1}$, $f_{res0}$ for each of the five possible states are calculated as follows:
Inserted in the resonance frequency formula, the following results:
For four intact capacitors:

$$f_{res4} = \frac{800}{\sqrt{\frac{1}{4}C}} \text{ [Hz]} = 673 \text{ MHz}$$

For three intact capacitors:

$$f_{res3} = \frac{800}{\sqrt{\frac{1}{3}C}} \text{ [Hz]} = 581 \text{ MHz}$$

For two intact capacitors:

$$f_{res2} = \frac{800}{\sqrt{\frac{1}{2}C}} \text{ [Hz]} = 475 \text{ MHz}$$

For one intact capacitor:

$$f_{res1} = \frac{800}{\sqrt{\frac{1}{1}C}} \text{ [Hz]} = 336 \text{ MHz}$$

For no intact capacitors: $f_{res4}$=0 Hz
The following statements thus result on the basis of the ascertained natural frequency of the oscillating circuit configuration:
  a stent in which no capacitor is defective responds at 673 Mhz.
  a stent having one defective and three intact capacitors responds at 581 Mhz.
  a stent having two defective and two intact capacitors responds at 475 Mhz.
  a stent having three defective capacitors and one intact responds at 336 Mhz.
  a stent having four defective capacitors does not permit any detection of the natural frequency.

The above situations and the corresponding natural frequencies are shown in FIGS. 2a-2e and FIG. 2f.

Figure 3A:
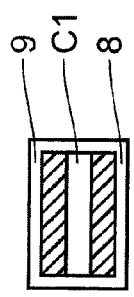
FIG. 3a shows a schematic cross-section through a strut of the stent as shown in FIG. 1.
Figure 3B:
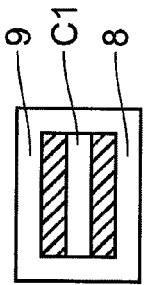
FIG. 3b shows a second schematic cross-section through a strut of the stent as shown in FIG. 1.
Figure 3C:
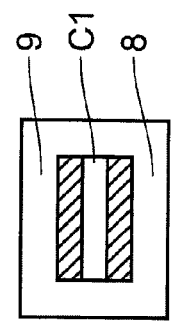
FIG. 3c shows a third schematic cross-section through a strut of the stent as shown in FIG. 1.
Figure 3D:
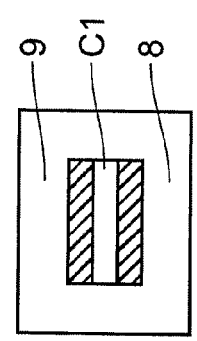
FIG. 3d shows a fourth schematic cross-section through a strut of the stent as shown in FIG. 1.

As is clear from FIGS. 3a-3d, the struts 2 of the stent 1 forming the capacitors C1 through C4 may be provided with insulation layers 8, 9 of different thicknesses. With identical biodegradable materials, the thin insulation layers 8, 9 in the exemplary embodiment from FIG. 3a are degraded significantly earlier than the increasingly thicker insulation layers 8, 9 in the other exemplary embodiments from FIGS. 3b-3d. The corresponding capacitor is thus short-circuited significantly earlier and thus removed from the oscillating circuit configuration 4.

Figure 4:
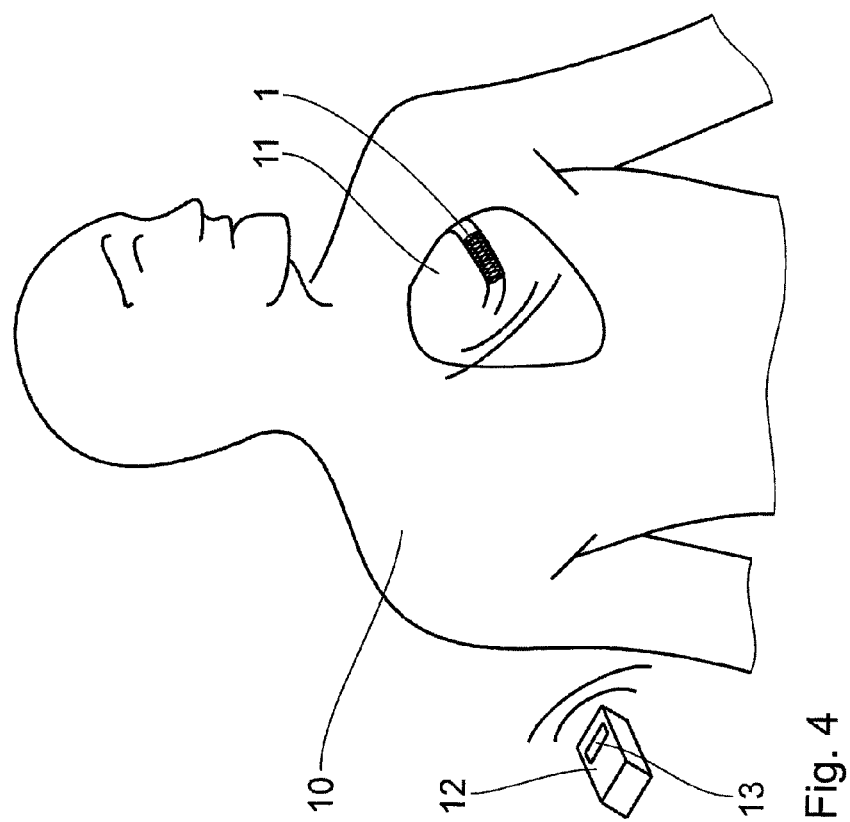
FIG. 4 shows a schematic view of a patient having an implanted stent and scanning device.
Figure 5C:
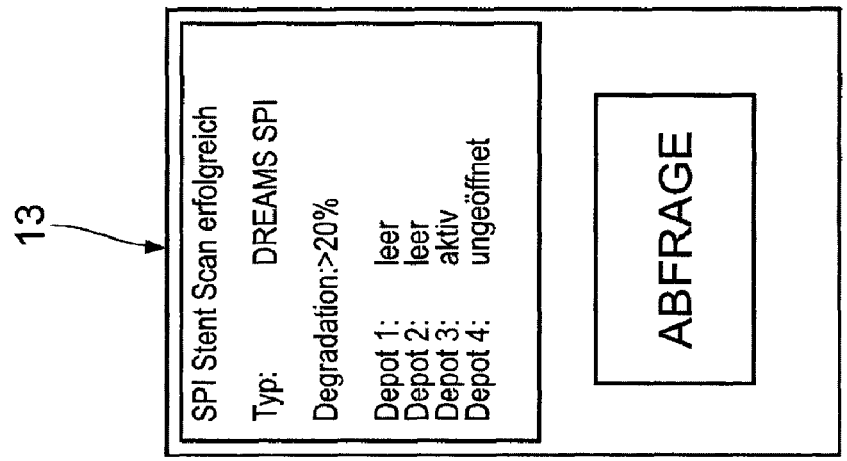
FIG. 5c shows an illustration of the display on the scanning device as a function of a third implanted stent.

A patient 10 is shown in FIG. 4, in whose heart 11 a stent 1 having oscillating circuit configuration 4 is implanted. The natural frequency of the oscillating circuit configuration 4 in the stent 1 may be scanned using an external scanning device 12. For this purpose, a frequency sweep generator is provided in the scanning device 12, which emits an electromagnetic radiation having a frequency range of 200 to 800 MHz, for example. Depending on the state of the individual capacitors C1 through C4 in the oscillating circuit configuration 4, the oscillating circuit will "respond" with one of the natural frequencies computed above, which is detectable by the scanning device 12 and convertible into a corresponding display. A display 13 is provided for this purpose on the scanning device 12, which is shown having various messages in FIGS. 5a-5c.

If the stent 1 is a nondegradable stent, this may be signaled by a natural frequency of the oscillating circuit configuration 4. If this natural frequency is ascertained by the scanning device 12, the model display "nondegradable SPI", i.e., "nondegradable stent" shown in FIG. 5a appears on the display 13.

Figure 5B:
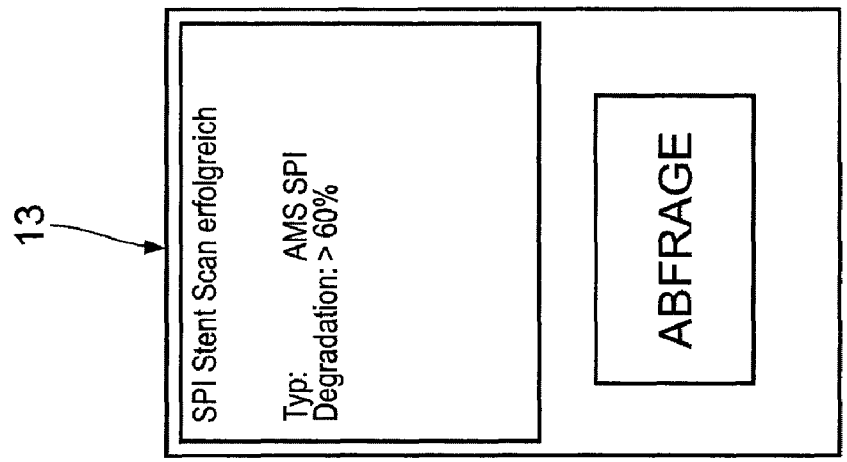
FIG. 5b shows an illustration of the display on the scanning device as a function of a second implanted stent.
Figure 5A:
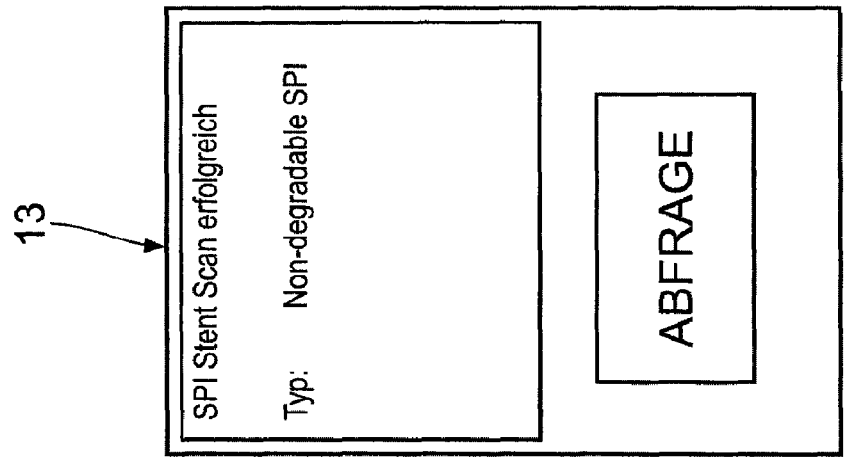
FIG. 5a shows a display on the scanning device as a function of one implanted stent.

If the stent 1 is a model of a biodegradable stent, this may again be detected via the measured natural frequencies and, as shown in FIG. 5b, be displayed accordingly in the form of model and degree of degradation information.

FIG. 5c shows the display in the display 13 with a stent 1 in which four medication depots are integrated. As explained in greater detail below on the basis of FIG. 10, the state of the particular depot may be detected via corresponding capacitors C1 through C4 and ascertained by the scanning device 12 on the basis of the measured natural frequency as a function of the short-circuit situation of the capacitors assigned to the medication depots.

Figure 6:
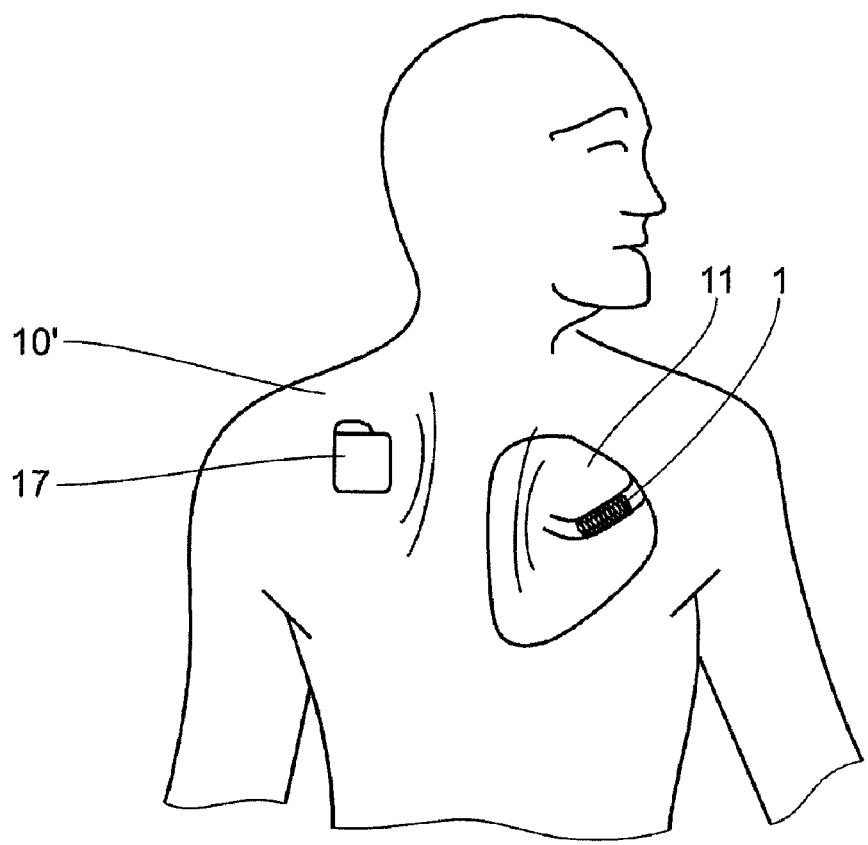
FIG. 6 shows a schematic view of a patient having an implanted stent and active medical implant.
Figure 8:
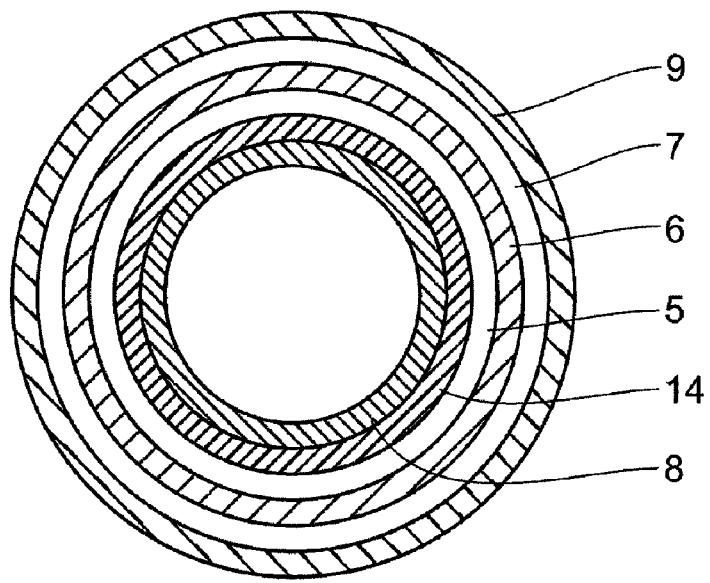
FIG. 8 shows a schematic cross-section through the stent.

Alternatively to the scanning device 12, the scan may also be executed by an active medical implant, such as a cardiac pacemaker 17, as indicated in FIG. 6. This transmits the ascertained information telemetrically to an external base device (not shown in greater detail).

A possible production path for the stent 1 having integrated oscillating circuit configuration 4 and its layered construction may be explained on the basis of FIGS. 7a-7f and FIG. 8 in very schematic form. The figures are greatly simplified, in that expansion elements typically provided in stents are not also illustrated, for example.

Figure 7A:
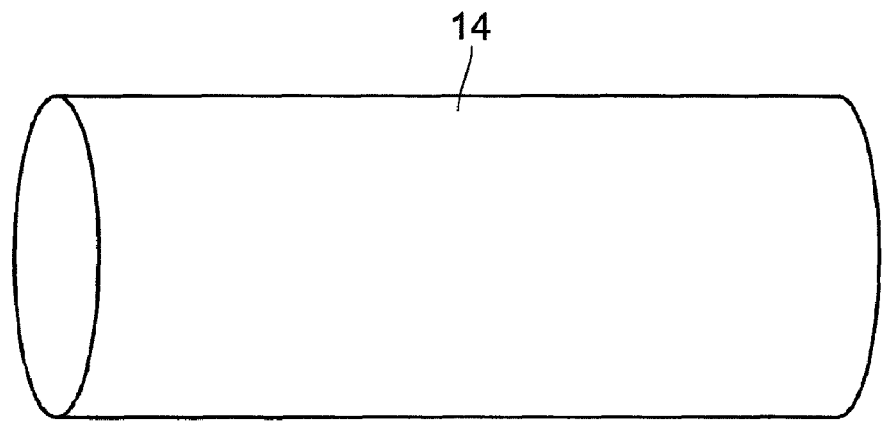
FIG. 7a shows a schematic diagram illustrating a production method for a stent having an oscillating circuit configuration.
Figure 7B:
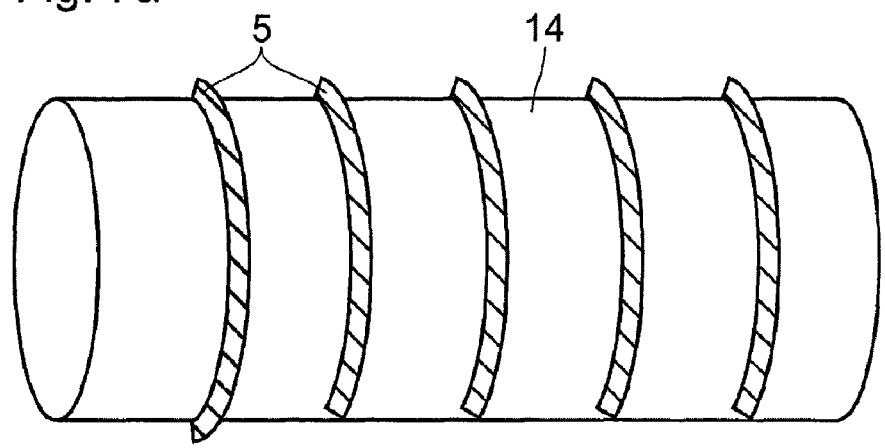
FIG. 7b shows a second schematic diagram illustrating a production method for a stent having an oscillating circuit configuration.
Figure 7C:
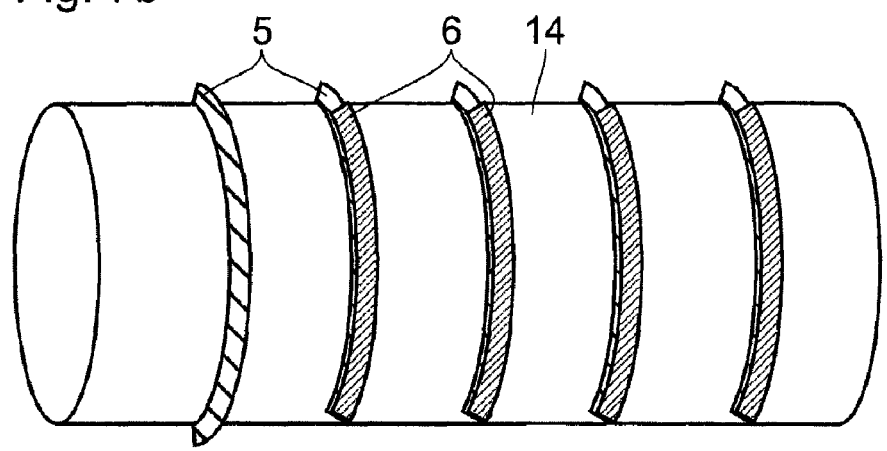
FIG. 7c shows a third schematic diagram illustrating a production method for a stent having an oscillating circuit configuration.
Figure 7D:
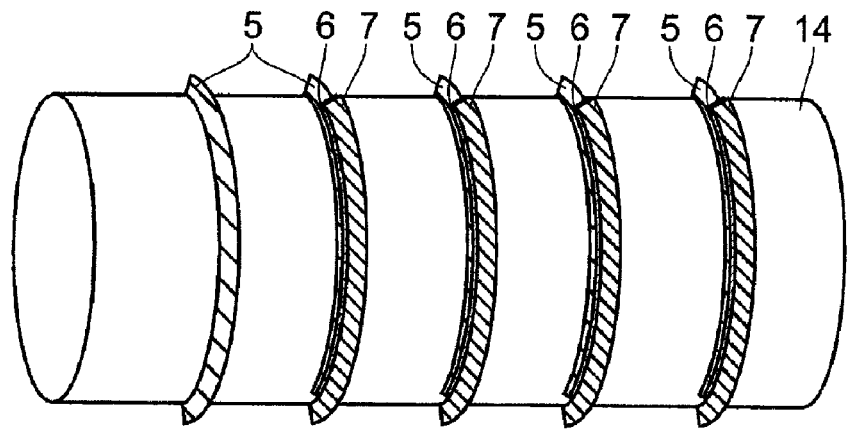
FIG. 7d shows a fourth schematic diagram illustrating a production method for a stent having an oscillating circuit configuration.

As shown in FIG. 7a, one begins with a tubular main body 14, which receives the following layers of the stent 1 and functions as the base structure of the particular strut in the finished product. Electrically conductive layers 5 in the form of partial rings are applied to this main body 14 running around the circumference U as printed conductors, which form the coil L and a capacitor pole of the capacitors C1 through C4 (FIG. 7b). An intermediate layer 6 made of a dielectric material is applied to a partial peripheral length of this internal electrically conductive layer 5 in the capacitors C1 through C4 (FIG. 7c). In the capacitors C1 through C4, an external electrically conductive layer 7 in the form of a partial ring is applied, again overlapping with this intermediate layer 6 (FIG. 7d).

Figure 7E:
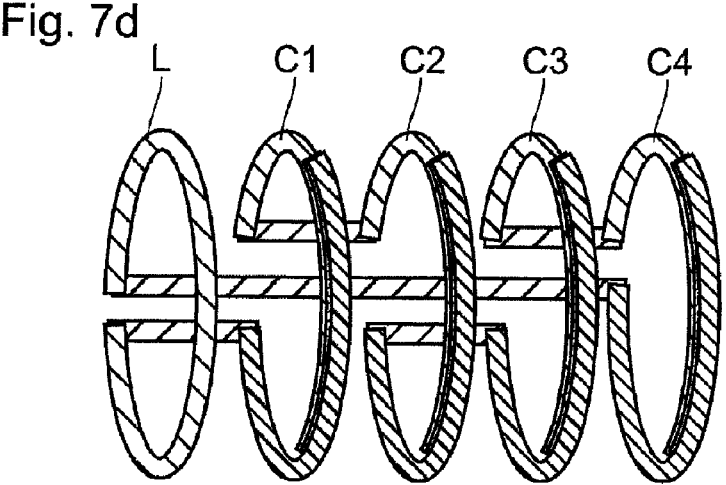
FIG. 7e shows a fifth schematic diagram illustrating a production method for a stent having an oscillating circuit configuration.
Figure 7F:
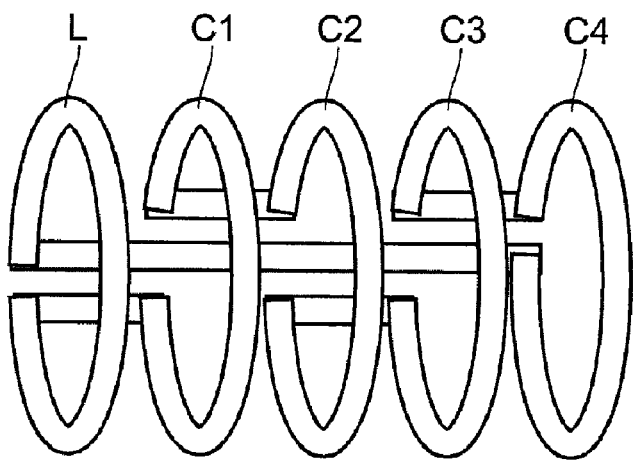
FIG. 7f shows a sixth schematic diagram illustrating a production method for a stent having an oscillating circuit configuration.

As is obvious from FIG. 7e, the actual stent structure is cut out of this blank and subsequently enclosed on all sides by insulation in the form of internal and external insulation layers 8, 9 (see FIG. 7f). Overall, the layered structure extremely schematically illustrated in cross-section in FIG. 8 results. The corresponding layers are, from the inside to the outside corresponding to the production method explained above, the internal insulation layer 8, the main body 14, the internal electrically conductive layer 5 as one capacitor pole, the dielectric intermediate layer 6, the external electrically conductive layer 7 as the second capacitor pole, and the external insulation layer 9.

If the insulation layers 8, 9, the main body 14, and the intermediate layer 6 comprise a uniform material on one hand and the two electrically conductive layers 5, 7 comprise an electrical conductor on the other hand, in the most favorable case, only two materials may be used for the stent, which are fundamentally known in stent designs.

Degradable, electrically nonconductive, biocompatible materials may be used for the main body 14 and insulation layers 8, 9. Biocompatible, electrically conductive materials are preferably to be used for the electrically conductive layers 5, 7 and the conductor loop for the inductor L, these being able to be materials already used for stents, for example, such as iron, magnesium, or their alloys. Electrically conductive polymers are also conceivable for the layers 5, 7.

Degradable, electrically nonconductive biocompatible materials may also be used for the intermediate layer 6.

Figure 9:
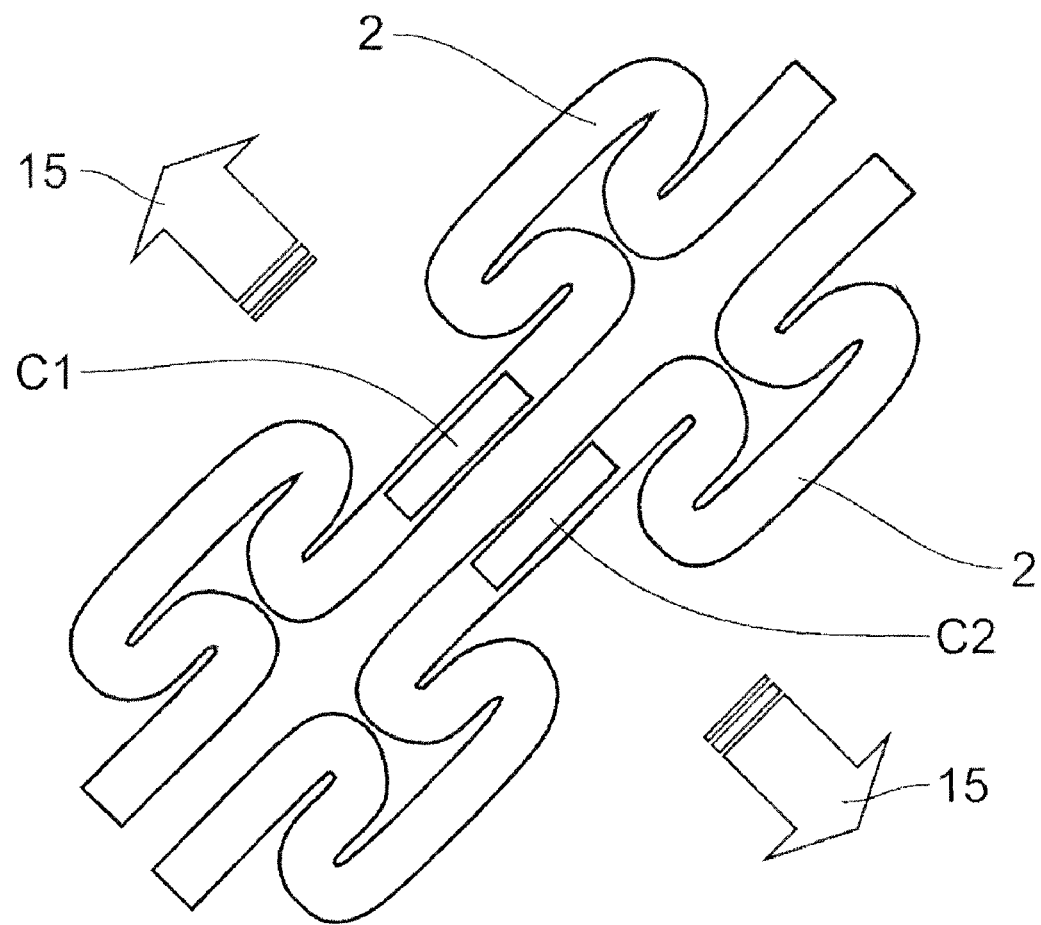
FIG. 9 shows a schematic view of two stent struts having indicated capacitors of the oscillating circuit configuration.

As is obvious from FIG. 9, the capacitors C1, C2 of the oscillating circuit configuration 4 may preferably be housed in less mechanically strained positions of the stent 1, i.e., in zones which are not deformed during the dilation (see arrows 15 in FIG. 9).

Figure 10C:
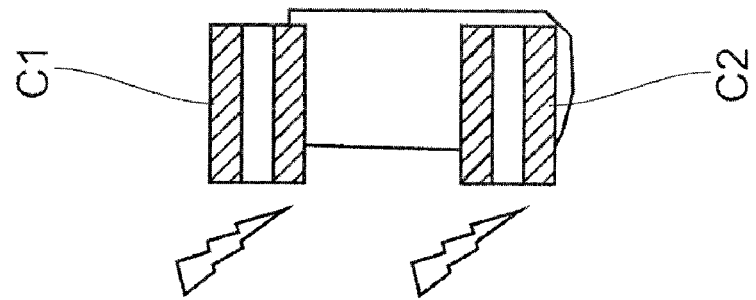
FIG. 10c shows a third cross-section through a strut of a stent having a medication depot and assigned oscillating circuit configurations.

The mode of operation of the oscillating circuit configuration 4 will now be explained in greater detail on the basis of FIGS. 10a-10c in connection with the detection of the activity of a medication depot in a stent. FIG. 10a shows a cross-section through a strut 2 of a stent 1 at the location of a medication depot 16, which is embedded jointly with two flanking capacitors C1, C2 in biodegradable insulation 8, 9. In the starting state from FIG. 10a, neither of the two capacitors C1, C2 is short-circuited and thus they both contribute to the oscillating circuit. A specific natural frequency of the oscillating circuit results.

Figure 10B:
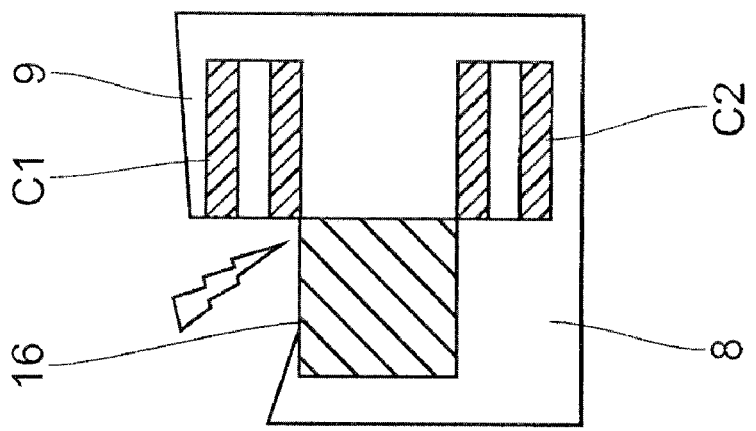
FIG. 10b shows another cross-section through a strut of a stent having a medication depot and assigned oscillating circuit configurations.
Figure 10A:
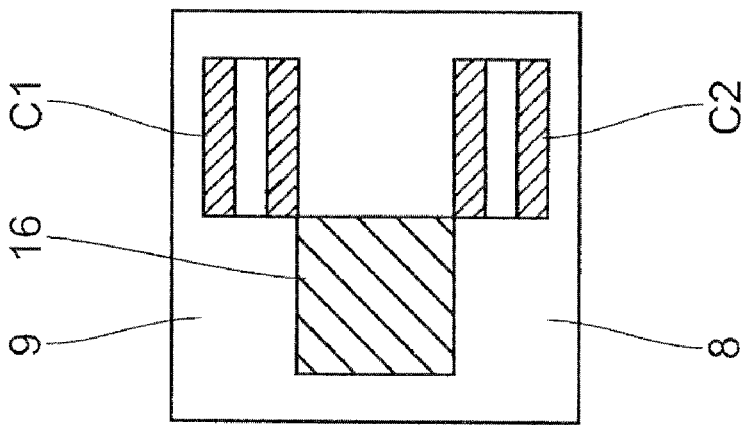
FIG. 10a shows a cross-section through a strut of a stent having a medication depot and assigned oscillating circuit configurations.

In FIG. 10b, the insulation layer 9 has already externally degraded in such a way that the medication depot 16 is exposed and thus an active ingredient delivery occurs. The capacitor C1 seated in the area of the degraded insulation layer 9 is thus also exposed and is short-circuited by the bodily fluid. The natural frequency of the oscillating circuit thus changes significantly, which may be ascertained by a scanning device 12. The corresponding jump in the natural frequency indicates that the medication release from the depot 16 is active.

Upon complete degradation of the medication depot 16 and corresponding decomposition of the insulation layers 8, 9, the second capacitor C2 is also exposed and thus short-circuited after a specific time, which in turn causes a significant jump in the natural frequency of the oscillating circuit 4. This is analyzed by the scanning device to mean that now the medication delivery from the depot 16 has completely run out and the depot is thus empty.

Finally, it is to be noted that a design of the capacitors C1 through C4 and the establishment of the natural frequency of the oscillating circuit formed therefrom may be performed by a change of the web width or length of the printed conductors forming the layers of the capacitor pole, by the use of different dielectric materials on a stent, or also a change of the dielectric material thickness. The latter may be implemented by an eccentric application of the dielectric material, for example.

Different series and parallel circuits of capacitors, coils, or also resistors are also conceivable to provide oscillating circuit configurations 4 with specific natural frequencies and changing behaviors upon an exposure of elements.

What is claimed is:

1. A medical implantable stent including a base structure having a passive electronic oscillating circuit, the circuit comprising:
   at least one inductor; and
   at least one capacitor,
   wherein both the at least one inductor and at least one capacitor are integrated in the base structure,
   wherein, when the electronic oscillating circuit is excited by electromagnetic radiation applied external to a body in which the stent has been implanted, the electronic oscillating circuit emits a signal having a natural frequency, and
   wherein the natural frequency of the oscillating circuit configuration signifies the model or the serial number of the implant.

2. A medical implantable stent including a base structure having a passive electronic oscillating circuit, the circuit comprising:
   at least one inductor; and
   at least one capacitor,
   wherein both the at least one inductor and at least one capacitor are integrated in the base structure,
   wherein, when the electronic oscillating circuit is excited by electromagnetic radiation applied external to a body in which the stent has been implanted, the electronic oscillating circuit emits a signal having a natural frequency, and
   wherein a change of the natural frequency of the oscillating circuit configuration after the implantation of the implant signifies damage to the base structure.

3. A medical implantable stent including a base structure having a passive electronic oscillating circuit, the circuit comprising:
   at least one inductor; and
   at least one capacitor,
   wherein both the at least one inductor and at least one capacitor are integrated in the base structure,
   wherein, when the electronic oscillating circuit is excited by electromagnetic radiation applied external to a body in which the stent has been implanted, the electronic oscillating circuit emits a signal having a natural frequency, and, wherein a change of the natural frequency of the oscillating circuit configuration after the implantation of the implant signifies the amount of biodegradation of the base structure.

4. The implant of claim 3, wherein the natural frequency is changeable by a short-circuit of the at least one capacitor, caused by the biodegradation of an insulation covering the oscillating circuit configuration and exposure of the capacitor to physiological, electrically conductive fluid flowing in the bodily lumen.

5. A medical implantable stent including a base structure having a passive electronic oscillating circuit, the circuit comprising:
- at least one inductor; and
- at least one capacitor,
- wherein both the at least one inductor and at least one capacitor are integrated in the base structure,
- wherein, when the electronic oscillating circuit is excited by electromagnetic radiation applied external to a body in which the stent has been implanted, the electronic oscillating circuit emits a signal having a natural frequency, and
- wherein the implant has a medication depot degrading with a time delay, and wherein a change of the natural frequency of the oscillating circuit configuration after the implantation of the implant signifies the status of a medication depot integrated in the implant.

6. The implant of claim 3, wherein the oscillating circuit includes a plurality of capacitors.

7. The implant of claim 1, wherein the inductor of the oscillating circuit is formed by an electrically conductive strut of the base structure.

8. The implant of claim 1, wherein the at least one capacitor of the oscillating circuit is formed by a layered construction of a strut of the base structure, the layered construction comprising an internal insulation layer, a first electrically conductive layer configured as a capacitor pole, an intermediate layer, implemented as a dielectric material, a second electrically conductive layer configured as a capacitor pole, and an external insulation layer.

9. The implant of claim 1, wherein the natural frequency of the oscillating circuit configuration is detectable by an external scanning device.

10. The implant of claim 1, wherein the oscillating circuit emits the signal with the natural frequency in response to electromagnetic radiation between a few kilohertz to 5 gigahertz.

11. The implant of claim 1, wherein the oscillating circuit emits the signal with the natural frequency in response to electromagnetic radiation between 300 MHz and 700 MHz.

12. The implant of claim 8, wherein the external insulation layer comprises a biodegradable material.

13. The implant of claim 6, wherein at least two of the plurality of capacitors have apacitance values that deviate from one another.

14. The implant of claim 2, wherein the inductor of the oscillating circuit is formed by an electrically conductive strut of the base structure.

15. The implant of claim 3, wherein the inductor of the oscillating circuit is formed by an electrically conductive strut of the base structure.

16. The implant of claim 5, wherein the inductor of the oscillating circuit is formed by an electrically conductive strut of the base structure.

17. The implant of claim 2, wherein the at least one capacitor of the oscillating circuit is formed by a layered construction of a strut of the base structure, the layered construction comprising an internal insulation layer, a first electrically conductive layer configured as a capacitor pole, an intermediate layer, implemented as a dielectric material, a second electrically conductive layer configured as a capacitor pole, and an external insulation layer.

18. The implant of claim 17, wherein the external insulation layer comprises a biodegradable material.

19. The implant of claim 2, wherein the signal emitted at the natural frequency by the oscillating circuit is of such a strength as to be detectable by an external scanning device.

20. The implant of claim 2, wherein the oscillating circuit emits the signal with the natural frequency in response to electromagnetic radiation between a few kilohertz to 5 gigahertz.

21. The implant of claim 2, wherein the oscillating circuit emits the signal with the natural frequency in response to electromagnetic radiation between 300 MHz and 700 MHz.

* * * * *